United States Patent [19]

Jordan

[11] 4,375,510

[45] Mar. 1, 1983

[54] **SELECTIVE MEDIUM COMPOSITION AND METHOD FOR THE DETECTION OF *ACTINOMYCES VISCOSUS* AND *ACTINOMYCES NAESLUNDII***

[75] Inventor: Harold V. Jordan, Wellesley Hills, Mass.

[73] Assignee: Forsyth Dental Infirmary for Children, Boston, Mass.

[21] Appl. No.: 240,769

[22] Filed: Mar. 5, 1981

[51] Int. Cl.³ .................. C12N 1/00; C12N 1/20; C12Q 1/04; C12R 1/04
[52] U.S. Cl. .................................. 435/34; 435/243; 435/253; 435/826
[58] Field of Search ............... 435/34, 243, 244, 253, 435/826

[56] References Cited

U.S. PATENT DOCUMENTS

| | | | |
|---|---|---|---|
| 3,278,393 | 10/1966 | Bahn et al. | 435/34 |
| 3,890,200 | 6/1975 | Jordan et al. | 435/253 |
| 4,140,580 | 2/1979 | Gibson et al. | 435/34 |
| 4,288,543 | 9/1981 | Sielaff et al. | 435/34 |

OTHER PUBLICATIONS

Beighton et al., J. Dent. Res., 55(5), 875–878 (1976).
Bibby et al., J. Inf. Dis., 69, 148–154 (1941).
Ellen et al., J. Clin. Microbiol., 2(4), 305–310 (1975).
Howell et al., J. Bact., 78, 82–95 (1959).
Kornman et al., J. Clin. Microbiol., 7(6), 514–518 (1978).
Pine et al., J. Lab. and Clin. Med., 54, 107–114 (1959).
Rosebury et al., J. Inf. Dis., 74, 131–143 (1944).
Fung et al., Health Lab. Science, 14(4), 273–278 (1977).
Zylber et al., J. Dent. Res., 59, Special Issue A, Abstract 898, 492, Mar. 1980.
Howell et al., J. Dent. Res., 41(5), 1050–1059 (1962).

*Primary Examiner*—Esther M. Kepplinger
*Attorney, Agent, or Firm*—Crowley, Richard P.

[57] ABSTRACT

A selective medium composition for the growth and detection of *Actinomyces viscosus* or *Actinomyces naeslundii*, which composition comprises: a solid medium selective to induce the growth of *Actinomyces viscosus* or *Actinomyces naeslundii;* a nutrient agent to induce the substantial growth of *Actinomyces viscosus* or *Actinomyces naeslundii;* a cadmium compound; a fluoride compound; a flavine compound; and the cadmium compound, the fluoride compound and the flavine compound all present in a concentration sufficient to inhibit the substantially full growth of interfering microorganisms, but in a concentration insufficient to inhibit the substantial growth of *Actinomyces viscosus* or *Actinomyces naeslundii.*

29 Claims, No Drawings

SELECTIVE MEDIUM COMPOSITION AND METHOD FOR THE DETECTION OF *ACTINOMYCES VISCOSUS* AND *ACTINOMYCES NAESLUNDII*

ACKNOWLEDGEMENT

Financial support was provided by Public Health Service Grant DE-02847 from the National Institute of Dental Research.

BACKGROUND OF THE INVENTION

The Actinomyces constitute a significant proportion of the complex microbial flora that inhabits the human oral cavity.[16, 3] The more facultative to aerobic species within this genus, *A. viscosus* and *A. naeslundii* have become the subject of increasing study within the past two decades, because of their suspected role in periodontal infections which affect the cervical areas of the teeth and the supporting tissues.[13, 22, 14] Clinical studies on the relationship of these organisms to oral disease and to the oral ecology in general have been hampered by the lack of reliable culture techniques. Differential media have been described in recent years for the selective cultivation of oral Actinomyces from clinical samples.[6, 1, 15] However, these media, which rely on either fluoride or cadmium to supress other members of the gram-positive oral flora, can be inhibitory to some strains of Actinomyces and are only partially selective.

The present invention describes the development of a practical selective medium for the detection and enumeration of *A. viscosus* and *A. naeslundii*. Improved recovery of these two species, as well as greater selectivity of the medium, was attained by the use of a combination of selective agents.

SUMMARY OF THE INVENTION

My invention concerns a novel and unique medium composition for the selective growth and detection of *Actinomyces viscosus* and *Actinomyces naeslundii*, the process of preparing the composition, and the method of using the medium composition for the growth, detection and enumeration of *Actinomyces viscosus* and *Actinomyces naeslundii*.

In particular, my invention relates to a selective medium composition which employs a combination of inhibitory agents for other microorganisms, with a medium and nutrient to induce the growth of *A. viscosus* and *A. naeslundii*, particularly from samples taken from the oral cavity.

My selective medium comprises: a solid medium selective to induce the growth for *A. viscosus* or *A. naeslundii*; a nutrient agent to induce the substantial growth of *A. viscosus* or *A. naeslundii*; a cadmium compound; a fluoride compound; a flavine compound; and the cadmium compound, the fluoride compound and the flavine compound all present in a concentration sufficient to inhibit the substantially full growth of interfering microorganisms, but in a concentration insufficient to inhibit the substantial growth of *A. viscosus* or *A. naeslundii*.

My medium composition provides the dentist, dental researcher or others with a simple means to detect *A. viscosus* or *A. naeslundii*, by culturing a sample from any part of the oral cavity, including saliva, to provide information relative to dental disease, such as periodontal disease, of the patient. My selective medium can be employed for other purposes and with other microorganism samples to grow selectively *A. viscosus* and *A. naeslundii*.

The particular agents employed and the concentration ranges of these agents in the composition may vary, depending upon the microorganism samples employed and the *A. viscosus* or *A. naeslundii* or combinations to be detected, but the inhibitory agents in combination may range, for example, from about 30 to 150 mg per liter.

The medium selected for my examples, to induce the growth of *A. viscosus* and *A. naeslundii*, was a solid agar medium containing a suitable nutrient agent, which medium is available as a commercial culture medium and which is selective for the growth of microorganisms, particularly for *A. viscosus* and *A. naeslundii*. However, it is recognized and is within the scope of my invention to employ any support medium and nutrient agent which is selective for the growth of the selected microorganisms to be detected.

A solid agar medium typically may contain a nutrient agent to induce the full growth of both *A. viscosus* and *A. naeslundii*, such as Trypticase Soy broth, beef extract, starch, brain-heart infusion, and other nutrients, alone or in combination. Such nutrient agents are present in a concentration to induce growth, such as 10 to 50 grams per liter of medium composition; for example, 20 to 35 grams per liter.

Optionally and preferably, my medium composition also may include a saccharide, such as a mono or di saccharide, such as glucose, fructose, sucrose or combinations thereof, typically in a concentration up to about 10 grams per liter; for example 1 to 10 grams per liter.

One essential inhibitory agent of my composition comprises a cadmium compound, to provide cadmium in a concentration sufficient to inhibit the growth of interfering microorganisms in the sample, but in a concentration insufficient to inhibit the growth of the *A. viscosus* or *A. naeslundii*. The concentration of the cadmium compound to be employed will vary, depending, for example, on the sample and the cadmium compound employed, but typically, for a cadmium compound, such as cadmium sulfate or its equivalent, would range from 2 up to 40 mg per liter, such as 10 to 50 mg per liter. The cadmium compound employed may be an organic or inorganic compound which provides cadmium, such as a cadmium acid salt ionic compound, such as cadmium sulfate, cadmium nitrate, cadmium acetate, etc.

Another essential inhibitory agent of my composition comprises a fluoride compound. As with the cadmium compound, the concentration of the fluoride compound may vary, but typically, for a fluoride compound, such as sodium fluoride, the concentration may fange from 30 to 250 mg per liter; for example, 50 to 100 mg per liter. The fluoride compound employed may be any organic or inorganic compound which provides fluoride, such as a fluoride acid salt, such as an alkali or alkaline earth fluoride, such as sodium fluoride, potassium fluoride, ammonium fluoride, calcium fluoride, etc.

A further essential inhibitory agent of my composition comprises a flavine or flavine-like compound. As with the other inhibitory agents, the concentration may vary, but typically, for a flavine compound, such as neutral acriflavine, the concentration may range from about 0.5 up to about 5.0 mg per liter; for example, 1.125 to about 2.25 mg per liter. The flavine compound may be any one of the flavine-type or flavine-dye series compound, particularly the amino alkyl acridinium halides, such as the mono and di amino, mono, di or tri methyl acridinium halides, such as neutral acriflavine. The three essential inhibitory agents—the cadmium, the fluoride and the flavine—may be varied in concentration, so as to inhibit undesired microorganism growth, but not to prevent substantial growth of the *A. viscosus* or *A. naeslundii*.

Optionally and preferably, my medium composition also includes an inhibitory agent which inhibits the growth of the Neisseria microorganisms; for example, a compound which contains tellurium, such as a tellurite compound; that is, a tellurium oxide compound, and typically an alkali metal or alkaline earth tellurite and combinations thereof, such as potassium, sodium or calcium tellurite. The concentration of the tellurite compound may vary, but should be sufficient to inhibit the growth in the medium composition of the Neisseria microorganisms. Typically with potassium tellurite, the concentration may range from about 0.5 to 5.0 mg per liter; for example, 1.5 to 3.0 mg per liter.

Optionally and preferably, my medium composition also includes an inhibitory agent which inhibits the growth of gram-negative microorganisms in the medium composition, such as a fuchsin compound or similar dye-like compounds, or antibiotics, such as polymyxin. The concentration of the gram-negative inhibitory agent may vary; however, typically, with an inhibitory compound like basic fuchsin, the concentration may range from about 0.1 to 2.0 mg per liter; for example, 0.15 to 0.50 mg per liter.

Optionally and preferably, my medium composition also may include a detoxifying agent, to enhance growth of the *A. viscosus* and *A. naeslundii*, such as the use of proteins, starch and particularly animal or human blood. Typically, the concentration of the agent may vary, but typically, with sheep's blood, may range from about 5 to 100 ml per liter; for example, 30 to 80 ml per liter.

My medium composition is useful in the growth and subsequent identification of *A. viscosus* and *A. naeslundii* from any microorganism sample, but finds particular utility in the detection of *A. viscosus* and *A. naeslundii* samples from the oral cavity of a patient related to the detection and treatment of periodontal disease.

My invention will be described for the purpose of illustration only in connection with certain embodiments and examples; however, it is recognized that those persons skilled in the art may make various changes in the described medium composition, all within the spirit and scope of my invention.

DESCRIPTION OF THE EMBODIMENTS

Materials and Methods

Preliminary studies were conducted, in order to select a suitable nutritional medium and growth conditions for subsequent screening of selective agents. Reference strains of *A viscosus* were tested for comparative growth on Trypticase Soy agar (BBL, Cockeysville, Md.), brain-heart infusion agar (Difco, Detroit, Mich.), Actinomyces agar (Difco, Detroit, Mich.), and Garrod's beef extract starch agar.[11, 19] The nine reference strains were: 19246, T14, W1838, M100, W1822, W1526, WVU626, T6 and RF7. The first seven strains are serotype 2 of human origin and the later two are serotype 1 strains of animal origin. Criteria used to evaluate these media included relative numbers of colonies, as well as size and appearance of the colonies.

Growth on these media was compared under anaerobic conditions (80% $N_2$, 10% $H_2$, 10% $CO_2$) versus aerobic conditions (90% air, 10% $CO_2$). All plates were incubated at 37° C. for 4 days.

On the basis of this initial comparison, Trypticase Soy agar containing 0.5% glucose was found to be equal to or superior to the other media in supporting growth of *A. viscosus*. Subsequent experiments indicated that improved colony size could be obtained on medium based on the formulation of Trypticase Soy broth (BBL) with glucose increased to 0.75% and with 1.5% agar added. Incubation under the air-$CO_2$ atmosphere was found to be adequate for the growth of *A. viscosus* reference strains.[6]

Since the commercial Actinomyces agar was found to be inhibitory to all *A. viscosus* reference strains tested, experiments were conducted to determine the basis of this inhibition. A simulated Actinomyces agar was prepared in the laboratory using the individual ingredients. Deletions were then carried out, in order to identify the inhibitory factor(s) in Actinomyces agar.

The known selective agents, cadmium and fluoride, were tested, in order to determine concentrations that would be noninhibitory to reference strains of *A. viscosus*, when added to the Trypticase Soy basal medium. Inhibition was recorded both in terms of colony numbers, as well as colony size and appearance. Preliminary studies had indicated that some strains of *A. viscosus* were sensitive to the concentrations of cadmium sulfate and sodium fluoride employed in CNAC-20 medium[6] and FC medium,[1] respectively. These and other potential selective agents were titrated against the battery of *A. viscosus* reference strains. Differential sensitivities of the agents were determined using six strains of oral streptococci. These were: *Streptococcus mutans*, 1B and 10449, *Streptococcus sanguis*, Di and 34, and *Streptococcus salivarius*, Vi and CMI. The streptococci were used for primary screening of selective agents, since they represent the most numerous group of gram-positive organisms likely to be encountered in oral samples.

Appropriate dilutions of Trypticase Soy broth cultures of the reference strains were plated on the test media containing the inhibitors and incubated at 37° C. under an atmosphere of 90% air, 10% $CO_2$, for 4 days. These growth conditions were employed for all of the inhibitors tested.

A differential sensitivity to one of the flavine dyes had been noted previously between *A. viscosus* and certain oral streptococci (Jordan and Gold, unpublished data). Neutral acriflavine (ICN, Plainview, N.Y.), a mixture of 2, 8 diamino-10-methyl acridinium chloride and 2, 8 diaminoacridine, was tested against the nine reference strains of *A. viscosus* and the six reference strains of oral streptococci, in order to establish an optimal selective concentration of this agent.

Tellurite was considered as a selective agent, because of the known differential sensitivities of various members of the oral-pharyngeal flora to this agent.[23] Bibby and Knighton[2] had isolated Actinomyces on a tellurite-containing medium. An initial screening of *A. viscosus* strains for their sensitivity to potassium tellurite revealed that the minimal inhibitory concentration was in the range of 1 to 5 µgm/ml. Although this concentration could be tolerated by the oral streptococci tested, it was observed that a strain of oral Neisseria (Keyes, P.H. and McCabe, R.M., Proceedings Int. Ass. Dental Res. Abst. 649, 1971) was inhibited. Accordingly, six oral isolates, with the characteristics of Neisseria, were compared to *A. viscosus* reference strains for their tolerance to potassium tellurite, in order to establish a critical selective concentration.

Basic fuchsin was used previously in an Actinomyces isolation medium at a concentration of 1 to 1,000,000 to suppress gram-negative bacteria.[12] This inhibitory dye was titrated in the Trypticase Soy basal medium, to establish a level that was suitable for the growth of the reference strains of *A. viscosus*.

A composite medium was formulated which contained all selective agents added to the Trypticase Soy basal medium at the highest concentrations that were noninhibitory for *A. viscosus* reference strains. The composition of CFAT is given in Table I.

In the original formulation of CFAT agar, neutral acriflavine was added to a concentration of 1.13 μgm/ml (Zylber, L. and Jordan, H., J. Dent. Res. 59: Special Issue A, Abst. 898, 1980). For convenience, this since has been rounded off to 1.20 μgm/ml. Subsequent tests have demonstrated no adverse effects on the growth of reference strains of Actinomyces.

Initial nutritional experiments with Trypticase Soy basal medium did not show a requirement for blood by the *A. viscosus* reference strains. However, later experiments with clinical samples indicated improved colony development from some samples when blood was added. For this reason, 5% defibrinated sheep blood has been included in the medium.

Although the selective concentrations of the inhibitors were established initially using the nine *A. viscosus* reference strains, the growth of five *A. naeslundii* reference strains on CFAT agar was subsequently checked, because of the similarity of these two species.

The CFAT composite medium was compared to CNAC-20 medium[6] and FC medium[1] for its ability to support the selective recovery of *A. viscosus* from clinical material. The cadmium-containing medium of Kornman and Loesche[15] was not included in this comparison. Dental plaque was obtained from accessible surfaces of the first and second molars of twenty-two laboratory workers and dental students. The samples were collected into VMGII transport medium[18], agitated for 30 seconds on a vortex mixer, and appropriate dilutions were plated out on the three selective media. The plates were incubated at 37° C. under an atmosphere of 90% air, 10% $CO_2$. After 4 days incubation, the plates were examined, and numbers of Actinomyces, as well as other types of oral bacteria, were recorded.

Prior to the actual comparative study, pilot experiments were conducted with the three media, to establish the types of organisms likely to be encountered. Initial identification of the different bacterial types were based on colonial appearance, gram strains and determination of major characteristics necessary for presumptive generic classification. Representative colonial types were then isolated randomly from the three media and identified according to standard methods.[4] A total of 130 isolates obtained during the pilot trials were characterized, usually to the species level, in this way. Reference strains of the following organisms were included in the identification procedures for comparison: *A. viscosus, A. naeslundii, S. mutans, S. sanguis, S. salivarius, Bacterionema matruchotii, Rothia dentocariosa*, Neissera and Aerococcus.

In the course of recording comparative bacterial counts on the three media, random isolates were spot-checked to confirm their presumptive identification, as described previously.

RESULTS

Reference strains of *A. viscosus* grew well on either Trypticase Soy basal medium, which contained added glucose, or brain-heart infusion agar or Garrod's medium. Differences in growth on the three media were insignificant, except that colony numbers of M100 and 19246 were decreased on Garrod's medium. None of the *A. viscosus* strains grew on Actinomyces agar under an atmosphere of 90% air, 10% $CO_2$. The inhibitory properties of this medium appear to be due, at least in part, to the high concentration (0.11 M) of $KH_2PO_4$. When Actinomyces agar was formulated to contain $KH_2PO_4$ at the same molar concentration as in the Trypticase Soy basal medium (0.014 M), full growth of the reference strains occurred. Addition of phosphate to Trypticase Soy basal medium up to a final concentration of 0.11 M completely inhibited the reference strains. Deletion of $(NH_4)_2SO_4$ from Actinomyces agar resulted in improved growth for most strains. However, addition of this compound to Trypticase Soy basal medium at the same concentration did not inhibit growth. All of these results were obtained under aerobic growth conditions. Actinomyces agar supported full growth of the reference strains of *A. viscosus* and *A. naeslundii* were incubated anaerobically.

The concentration of cadmium sulfate employed in CNAC-20 medium did not allow full growth of all of the *A. viscosus* reference strains. CNAC-20 contains 20 μgm/ml 3 $CdSO_4$.8 $H_2O$, which is equivalent to 16.2 μgm/ml $CdSO_2$. The maximum concentration of $CdSO_4$ that did not inhibit any of the *A. viscosus* reference strains of human origin (serotype 2) tested in the present study was 13 μgm/ml. This concentration was found to be inhibitory to most of the streptococcal reference strains, except for one strain of *S. sanguis* and one strain of *S. salivarius*, which grew with reduced colony size. The serotype 1 animal strains of *A. viscosus* (RF7, T6) were more sensitive to cadmium than the serotype 2 human strains. This differential sensitivity was investigated further. Additional strains of catalase positive, diphtheroidal organisms, with morphological and biochemical properties of *A. viscosus*, were isolated from Syrian hamsters maintained at the Forsyth Dental Center animal facility. These isolates were tested for cadmium tolerance and, like the two reference animal strains, were found to be more sensitive than the strains of human origin (Table 2). The freshly isolated animal strains were even more sensitive to cadmium than the two reference animal strains.

The relative resistance of *A. viscosus* to fluoride reported by Beighton and Colman[1] was confirmed. The two reference strains of each of *Strep. sanguis* and *Strep. mutans* were completely inhibited at 250 μgm/ml NaF, the concentration employed in FC medium. The two reference strains of *Strep. salivarius* showed only limited growth at this concentration. Although the reference strains of *A. viscosus* grew at 250 μgm/ml NaF, colony size and, in a few cases, colony numbers were reduced. Full growth of all strains, without a reduction in colony size, was attained at a concentration of 80 μgm/ml NaF. This concentration of NaF did not completely inhibit the reference strains of streptococci. Partial growth of all strains occurred at 100 μgm/ml. The two strains of *Strep. salivarius* were the most resistant of the streptococci and exhibited significant growth at 200 μgm/ml.

Neutral acriflavine showed a significant differential inhibitory effect against the reference strains of viridans streptococci compared to *A. viscosus*. The results are presented in Table 3. Five of the six streptococcal strains were completely inhibited at an acriflavine concentration of 1.125 µgm/ml and one *S. sanguis* strain showed limited growth. The *A. viscosus* reference strains were not inhibited at this concentration, and most grew well at 1.50 µgm/ml. Strains W1528 and WVU626 were not inhibited at a concentration of 2.25 µgm/ml.

Basic fuchsin was found to be inhibitory to some strains of *A. viscosus* at the concentration used in Garrod's medium, and, therefore, the level of this agent was reduced to 0.25 µgm/ml. The maximum concentration of potassium tellurite that allowed full growh of all strains of *A. viscosus* was 2.5 µgm/ml. Strains of oral Neisseria tested were completely inhibited at this concentration.

The composite selective medium (CFAT), with the composition given in Table 1, supported full growth of the *A. viscosus* reference strains. Three *A. naeslundii* reference strains (12104, 6–60b, 6–126c) grew on this medium; however, two strains (N16, 4A05) did not grow.

Comparison of the three selective media revealed significant differences in recovery of Actinomyces from clinical material, as well as in selectivity of the media in relation to extraneous organisms. Table 4 shows the frequency of isolation of Actinomyces and other competing organisms from the 22 clinical samples. *A. viscosus* was recovered from all samples on CFAT and FC media and from 64% of samples on CNAC-20. Organisms identified as *A. naeslundii* were recovered from most samples on CFAT and FC media, but only from about one-third of the samples of CNAC-20. The major groups of extraneous organisms, which occurred in varying proportions on the different media, were identified as Rothia, Aerococcus, Neisseria, streptococci, Bacterionema and yeasts. The selectivity of CFAT relative to these interfering organisms was clearly better than the other two media.

Relative populations of Actinomyces and the different competing organisms on the three isolation media are given in Table 5. Numbers of Actinomyces recovered on CFAT were considerably higher than on the other two media. The major interfering organisms on this medium were Aerococcus and Rothia. Although the numbers of these organisms were low, the colonies were often similar in size and appearance to Actinomyces. Streptococcal colonies on CFAT were very small, and the relatively low numbers did not present a problem. The FC and CNAC-20 media were less selective and supported the growth of significant numbers of interfering organisms. A lower porportion of *A. naeslundii*, in relation to *A. viscosus*, was recovered on CNAC-20 compared to the other media. Large numbers of small, grey, translucent colonies on CNAC-20 were identified as streptococci.

DISCUSSION

Various media have been used in the past for the isolation of Actinomyces from the mouth and from actinomycotic lesions.[2, 8, 11, 19, 20] A major concern of these early workers appears to have been the selection of media that would support adequately the growth of fastidious Actinomyces. The media used in these studies were not selective in relation to the bulk of the competing flora; thus, the isolation and identification of Actinomyces, particularly from the complex oral flora, could be a laborious and time-consuming process. Differential isolation media described in recent years[1, 6, 15], which depend on the selective inhibition of extraneous gram-positive organisms by cadmium or fluoride, represent an important advance in the detection of oral Actinomyces by cultural procedures. In the present study, the relative resistance of *A. viscosus* and *A. naeslundii* to cadmium and fluoride, compared to the streptococci, has been confirmed. However, partial inhibition of some Actinomyces strains was noted at the concentrations employed in CNAC-20 and FC media. Use of these agents at reduced concentrations in combination with acriflavin appears adequate for the control of most of the streptococcal flora.

Greater cadmium sensitivity of the animal strains of *A. viscosus*, compared to human strains, is of interest taxonomically. This could illustrate another fundamental difference between strains of animal and human origin, in addition to the known serologic[9] and genetic (Coykendall and Munzenmaier, Proceedings Int. Assn. Dent. Res. Abst. 1120, 1978) differences. On a practical level, this suggests that the CFAT medium, as presently formulated, would not be suitable for investigating natural *A. viscosus* infections in rodents.

With currently available culture techniques, it is necessary to evaluate *A. viscosus* and *A. naeslundii* populations in clinical material simultaneously. The similarity of these two species is well documented.[7, 9, 10] Gerencser and Slack[9] pointed out that the similarities between the two species were so great that *A. viscosus* may be considered a catalase positive variant of *A. naeslundii*. However, they felt that adequate differences existed to maintain them as separate species at that time. The present study demonstrates that this similarity between the two species also includes their response to different types of selective agents.

Since the intraoral pathogenicity of *A. viscosus* and *A. naeslundii* in experimental animals is similar and both are prominent members of the gingival plaque flora, it may be an advantage to monitor populations of the two species together. However, there is some evidence that the sequence of colonization of the human mouth by these two species is different.[5] This suggests that there may be situations where it would be desirable to examine the oral populations of either species by itself. At present, differentiation of these species in studies of this type depends on the catalase reaction[5] or on certain immunological procedures.[17, 21] The presence of blood in CFAT agar eliminates the possibility of using the Catalase reaction directly on this medium.

The CFAT medium appears to represent a significant improvement over presently available media for the selective cultivation of *A. viscosus and A. naeslundii* in clinical material, although some strains of the latter species may not be recovered. Both species can be recovered in higher numbers, whereas organisms, such as Neisseria, Bacterionema and yeasts, have been eliminated. Streptococci, which can be a major problem, have been reduced to insignificant numbers. Ellen and Balcerzak-Raczkowski[6] had reported the tendency of CNAC-20 to inhibit the growth of *A. naeslundii* and also to support the growth of some streptococci. This was confirmed in the present study. The aerobic organisms, Rothia and Aerococcus, which were encountered in significant numbers on FC and CNAC-20 media, have been reduced, but not eliminated, in CFAT. The use of a combination of selective agents at concentrations which are less inhibitory for *A. viscosus* and *A. naeslundii* appears to offer an advantage over single inhibitor media in supressing the extraneous gram-positive flora.

TABLE 1

Composition of a Selective Medium (CFAT) for *Actinomyces viscosus* and *Actinomyces naeslundii*.

| | Per Liter |
|---|---|
| Trypticase Soy broth (BBL)* | 30 gm |
| Glucose | 5 gm |
| Agar | 15 gm |
| Cadmium sulfate | 13 mg |
| Sodium fluoride | 80 mg |
| Neutral acriflavin | 1.20 mg |
| Potassium tellurite | 2.50 mg |
| Basic fuchsin | 0.25 mg |
| Defibrinated sheep blood | 50 ml |
| pH 7.3 | |

*contains about 2.5 grams per liter of glucose as provided

TABLE 2

Sensitivity of Rodent Strains of *Actinomyces viscosus* to Cadmium

| | CdSO$_4$ ($\mu$gm/ml)[a] | | | | |
|---|---|---|---|---|---|
| Strain No. | 6.5 | 5.0 | 2.5 | 1.25 | 0 |
| DH30 | 0 | 0 | 0 | 150 | 300 |
| DH16 | 0 | 0 | 0 | 50[b] | TNTC[c] |
| DH4 | 0 | 0 | 0 | 0 | TNTC |
| RF7 | 0 | 0 | 200[b] | 200[b] | 300 |
| T6 | 16[b] | 60[b] | 120[b] | 115[b] | 195 |

[a]final concentration in Trypticase Soy basel medium.
[b]reduced colony size.
[c]too numerous to count.
Results expressed as number of colonies per plate from equivalent dilutions.

TABLE 3

Differential Inhibition of *Actinomyces viscosus* and Oral Streptococci by Neutral Acriflavin.

| | Acriflavin ($\mu$gm/ml)[a] | | | | |
|---|---|---|---|---|---|
| Reference Strains | 2.25 | 1.75 | 1.50 | 1.125 | 0 |
| *S. sanguis* Di | 0 | 0 | 6 | 9 | 32 |
| *S. sanguis* 34 | 0 | 0 | 0 | 0 | 24 |
| *S. salivarius* Vi | 0 | 0 | 0 | 0 | TNTC[c] |
| *S. salivarius* CM1 | 0 | 0 | 0 | 0 | TNTC[c] |
| *S. mutans* 10449 | 0 | 0 | 0 | 0 | 192 |
| *S. mutans* IB | 0 | 0 | 0 | 0 | TNTC[c] |
| *A. viscosus* 19246 | 100[b] | 140[b] | 250 | 250 | 280 |
| *A. viscosus* RF7 | 130[b] | 120[b] | 90[b] | 200 | 200 |
| *A. viscosus* T14 | 32 | 108 | 80 | 110 | 114 |
| *A. viscosus* W1838 | 5 | 11 | 22 | 24 | 22 |
| *A. viscosus* M100 | 80[b] | 75 | 200 | 125 | 200 |
| *A. viscosus* T6 | 66 | 100 | 110 | 110 | 110 |
| *A. viscosus* W1822 | 28 | 30 | 45 | 40 | 53 |
| *A. viscosus* W1528 | 100 | 130 | 95 | 140 | 100 |
| *A. viscosus* WVU626 | 280 | 260 | 280 | 280 | 280 |

[a]final concentration in Trypticase Soy basal medium.
[b]reduced colony size.
[c]too numerous to count.
Results expressed as number of colonies per plate from equivalent dilutions.

TABLE 4

Frequency of Recovery of *Actinomyces viscosus*, *Actinomyces naeslundii*, and Extraneous Organisms on Three Isolation Media.

| Organism | CFAT | FC | CNAC-20 |
|---|---|---|---|
| *A. viscosus* | 100 | 100 | 64 |
| *A. naeslundii* | 95 | 82 | 32 |
| Streptococci | 9 | 32 | 95 |
| Rothia | 5 | 64 | 36 |
| Aerococcus | 100 | 100 | 100 |
| Bacterionema | 0 | 32 | 23 |
| Neisseria | 0 | 14 | 5 |
| Yeasts | 0 | 14 | 14 |

All values expressed as percent positive samples.

TABLE 5

Comparative Recovery of *Actinomyces viscosus*, *Actinomyces naeslundii*, and Extraneous Organisms on three Isolation Media.

| Organism | CFAT | FC | CNAC-20 |
|---|---|---|---|
| *A. viscosus* | 494 ± 166 (8–2630) | 102 ± 369 (1–790) | 21.7 ± 11.9 (0–210) |
| *A. naeslundii* | 325 ± 123 (0–2500) | 55.6 ± 294 (0–600) | 1.59 ± 1.39 (0–30) |
| Streptococci | 2.87 ± 2.86 (0–50) | 35.2 ± 13.6 (1–200) | 51.5 ± 11.4 (0–2000) |
| Rothia | 0.52 ± 3.48 (0–11) | 13.7 ± 7.31 (1–20) | 3.04 ± 9.85 (0–45) |
| Aerococcus | 134 ± 38.6 (0.2–600) | 176 ± 43.7 (2–610) | 3.70 ± 1.17 (2–20) |
| Bacterionema | 0 | 7 ± 4.37 (0–40) | 7.9 ± 3.77 (0–50) |
| Neisseria | 0 | 0.76 ± 0.49 (0–10) | .005 ± .005 (0–0.1) |
| Yeast | 0 | 1.60 ± 1.03 (0–30) | 1.20 ± 0.92 (0–20) |

Results expressed as mean ± standard error.
Numbers in parentheses indicate range of values.
All values × 10$^3$.

LITERATURE CITED

1. Beighton, D. and G. Colman. 1976. A medium for the isolation and enumeration of Actinomycetaceae from dental plaque. J. Dent. Res. 55: 875–878.

2. Bibby, B. G. and H. T. Knighton. 1941. The Actinomyces of the human mouth. J. Inf. Dis. 69: 148–154.

3. Bowden, G. H., J. M. Hardie, A. S. McKee, P. D. Marsh, E. D. Fillery and G. L. Slack. 1976. The microflora associated with developing carious lesions of the distal surfaces on the upper first premolars in 13–14 year old children. In: Proceedings "Microbial Aspects of Dental Caries". Eds Stiles, Loesche, and O'Brien. Sp. Supp. Microbiology Abstracts 1: 223–241.

4. Cowan, S. T. 1974. Cowan and Steel's manual for the identification of medical bacteria, 2nd Ed. Cambridge University Press, London.

5. Ellen, R. P. 1976. Establishment and distribution of *Actinomyces viscosus* and *Actinomyces naeslundii* in the human oral cavity. Infect. and Immun. 14, 1119–1124.

6. Ellen, R. P. and I. B. Balcerzak-Raczkowski. 1975. Differential medium for detecting dental plaque bacteria resembling *Actinomyces viscosus* and *Actinomyces naeslundii*. J. Clin. Microbial 2: 305–310.

7. Fillery, E. D., G. H. Bowden and J. M. Hardie. 1978. A Comparison of Strains of bacteria designated *Actinomyces viscosus* and *Actinomyces naeslundii*. Caries Res. 12: 299–312.

8. Garrod, L. P. 1952. Actinomycosis of the lung. Tubercle 33: 258–266.

9. Gerencser, M. A. and J. M. Slack. 1969. Identification of human strains of *Actinomyces viscosus*. Applied Microbiol. 18: 80–87.

10. Holmberg, K. and H. O. Hallander. 1973. Numerical taxonomy and laboratory identification of *Bacterimema matruchotti*, *Rothia dentocariosa*, *Actinomyces naeslundii*, *Actinomyces viscosus* and some related bacteria. J. Gen. Microbial. 76: 43–63.

11. Howell, A. Jr., W. C. Murphy III F. Paul, and R. M. Stephan. 1959. Oral strains of Actinomyces. J. Bact. 78: 82–95.

12. Howell, A., Jr., R. M. Stephan, and F. Paul. 1962. Prevalence of *Actinomyces israelii, A. naeslundii, Bacterionema matruchotii* and *Candida albicans* in selected areas of the oral cavity and saliva. J. Dent. Res. 41: 1050–1059.

13. Jordan, H. V. and P. H. Keyes. 1964. Aerobic, Gram-positive filamentous bacteria as etiologic agents of experimental periodontal disease in hamsters. Arch. Oral Biol. 9: 401–414.

14. Jordan, H. V., P. H. Keyes, and S. Bellack. 1972. Periodontal lesions in hamsters and gnotobiotic rats infected with *Actinomyces* of human origin. J. Periodont. Res. 7: 21–28.

15. Kornman, K. S. and W. J. Loesche. 1978. New medium for isolation of *Actinomyces viscosus* and *Actinomyces naeslundii* from dental plaque. J. Clin. Microbiol. 7: 514–518.

16. Loesche, W. J., R. N. Hockett, and S. A. Syed. 1972. The predominant cultivable flora of tooth surface plaque removed from institutionalized subjects. Arch. Oral Biol. 17: 1311–1325.

17. Marucha, P. T., P. H. Keyes, C. L. Wittenberger, and J. London. 1978. Rapid method of identification and enumeration of oral *Actinomyces*. Infect. and Immun. 21: 786–791.

18. Moller, A. J. R. 1966. Microbiological examination of root canals and periapical tissues of human teeth. Odont. Tidskr. 74: No. 5-6 special article.

19. Pine. L. and S. J. Watson. 1959. Evaluation of an isolation and maintenance medium for *Actinomyces species and related organisms*. J. Lab. and Clin. Med. 54: 107–114.

20. Rosebury, T., L. J. Epps, and A. R. Clark. 1944. A study of the isolation, cultivation and pathogenicity of *Actinomyces israelii* recovered from the human mouth and from actinomycosis in man. J. Inf. Dis. 74: 131–143.

21. Slack, J. M., S. Landfried, and M. A. Gerencser. 1971. Identification of *Actinomyces and related bacteria in dental calculus by the fluorescent antibody technique*. J. Dent. Res. 50: 78–82.

22. Socransky, S. S., C. Hubersak, and D. Propas. 1970. Induction of periodontal destruction in gnotobiotic rats by a human oral strain of *Actinomyces naeslundii*. Arch. Oral. Biol. 15: 993–995.

23. Wilson, G. S. and A. A. Miles. 1964. In: Topley and Wilson's Principles of Bacteriology and Immunology, 5th Ed. P. 1677–1679. The Williams and Wilkins Co., Batimore, Md.

What I claim is:

1. A selective medium composition for the growth and detection of *Actinomyces viscosus* or *Actinomyces naeslundii*, which composition comprises:
   (a) a solid medium selective to induce the growth of *Actinomyces viscosus* or *Actinomyces naeslundii*;
   (b) a nutrient agent to induce the substantial growth of *Actinomyces viscosus* or *Actinomyces naeslundii*;
   (c) a cadmium compound;
   (d) a fluoride compound;
   (e) a flavine compound; and
   (f) the cadmium compound, the fluoride compound and the flavine compound all present in a concentration sufficient to inhibit the substantially full growth of interfering microorganisms, but in a concentration insufficient to inhibit the substantial growth of *Actinomyces viscosus* or *Actinomyces naeslundii*.

2. The composition of claim 1 wherein the cadmium compound is cadmium sulfate present in a concentration of up to about 13 mg per liter.

3. The composition of claim 1 wherein the fluoride compound is sodium fluoride present in a concentration of up to about 250 mg per liter.

4. The composition of claim 1 wherein the flavine compound is acriflavine present in a concentration of up to about 2.25 mg per liter.

5. The composition of claim 4 wherein the flavine compound comprises an amino methyl acridinium halide.

6. The composition of claim 1 wherein the cadmium compound is a cadmium acid salt compound, the fluoride compound is an alkali metal salt fluoride and the flavine compound is acriflavine.

7. The composition of claim 1 wherein the solid medium is an agar medium.

8. The composition of claim 1 wherein the nutrient agent is selected from the group consisting of Trypticase Soy broth, brain heart infusion, beef extract and combinations thereof.

9. The composition of claim 1 wherein includes a saccharide compound.

10. The composition of claim 9 wherein the saccharide compound comprises glucose in a concentration of up to about 10 grams per liter.

11. The composition of claim 1 which includes a blood compound in a concentration to enhance the growth of the *Actinomyces viscosus* or *Actinomyces naeslundii*.

12. The composition of claim 11 wherein the blood comprises animal blood in a concentration of from about 5 to 100 ml per liter.

13. The composition of claim 1 which includes a tellurite compound in a concentration sufficient to inhibit the growth of *Neisseria* microorganisms.

14. The composition of claim 13 wherein the tellurite compound is an alkali metal tellurite compound in a concentration of from about 0.5 to 5.0 mg per liter.

15. The composition of claim 1 which includes an agent to inhibit the substantially full growth of gram-negative bacteria.

16. The composition of claim 15 wherein the agent comprises fuchsin in a concentration of from about 0.1 to 1.0 mg per liter.

17. The composition of claim 1 wherein the cadmium compound is present in a concentration of from about 2 to 50 mg per liter of composition.

18. The composition of claim 1 wherein the fluoride compound is present in a concentration of from about 30 to 250 mg per liter of composition.

19. The composition of claim 1 wherein the flavine compound is present in a concentration of from about 0.5 to 5.0 mg per liter of composition.

20. The composition of claim 1 wherein the nutrient agent is present in a concentration of from about 10 to 50 grams per liter of medium composition.

21. A selective medium composition for the growth and detection of *Actinomyces viscosus* or *Actinomyces naeslundii*, which composition comprises:

|  | Per Liter |
|---|---|
| Trypticase Soy broth | 10 gm to 50 gm |
| glucose | 1 gm to 10 gm |

-continued

| | Per Liter |
|---|---|
| agar | 10 gm to 50 gm |
| cadmium sulfate | 10 mg to 13 mg |
| sodium or potassium fluoride | 80 mg to 250 mg |
| neutral acriflavine | 1.125 mg to 2.50 mg |
| sodium or potassium tellurite | 1.0 mg to 5.0 mg |
| basic fuchsin | 0.1 mg to 1.0 mg |
| animal blood | 10 ml to 100 ml |

22. A selective medium composition for the growth and detection of *Actinomyces viscosus* or *Actinomyces naeslundii*, which composition comprises:

| | Per Liter |
|---|---|
| Trypticase Soy broth | about 30 gm |
| glucose | about 5 gm |
| agar | about 15 gm |
| cadmium sulfate | about 13 mg |
| sodium fluoride | about 80 mg |
| neutral acriflavine | about 1.20 mg |
| potassium tellurite | about 2.50 mg |
| basic fuchsin | about 0.25 mg |
| defibrinated sheep blood | about 50 ml |

23. A method for the selected growth of *Actinomyces viscosus* or *Actinomyces naeslundii*, which method comprises:
 (a) providing a selective medium composition for the growth and detection of *Actinomyces viscosus* or *Actinomyces naeslundii*, which composition comprises
  (i) a solid medium selective to induce the growth of *Actinomyces viscosus* or *Actinomyces naeslundii*,
  (ii) a nutrient agent to induce the substantial growth of *Actinomyces viscosus* or *Actinomyces naeslundii*,
  (iii) a cadmium compound,
  (iv) a fluoride compound,
  (v) a flavine compound, and
  (vi) the cadmium compound, the fluoride compound and the flavine compound all present in a concentration sufficient to inhibit the substantially full growth of interfering microorganisms, but in a concentration insufficient to inhibit the substantial growth of *Actinomyces viscosus* or *Actinomyces naeslundii*;
 (b) inoculating the medium with a selected microorganism; and
 (c) culturing the microorganism *Actinomyces viscosus* or *Actinomyces naeslundii* in the medium under aerobic conditions.

24. The method of claim 23 which comprises culturing the microorganism in an atmosphere of about 90% air and 10% $CO_2$.

25. The method of claim 23 wherein the medium composition comprises:

| | Per Liter |
|---|---|
| Trypticase Soy broth | 10 gm to 50 gm |
| glucose | 1 gm to 10 gm |
| agar | 10 gm to 50 gm |
| cadmium sulfate | 10 mg to 13 mg |
| sodium or potassium fluoride | 80 mg to 250 mg |
| neutral acriflavine | 1.125 mg to 2.50 mg |
| sodium or potassium tellurite | 1.0 mg to 5.0 mg |
| basic fuchsin | 0.1 mg to 1.0 mg |
| animal blood | 10 ml to 100 ml |

26. The method of claim 23 which includes inoculating the culture medium with a microorganism sample from the oral cavity of a patient.

27. A selective medium composition for the growth and detection of *Actinomyces viscosus* or *Actinomyces naeslundii*, which composition comprises:
 (a) a solid medium selective to induce the growth of *Actinomyces viscosus* or *Actinomyces naeslundii*;
 (b) a nutrient agent to induce the substantial growth of *Actinomyces viscosus* or *Actinomyces naeslundii*;
 (c) an acid salt cadmium compound in concentration of from about 2 to 50 mg per liter of the composition;
 (d) an alkali metal salt fluoride compound in a concentration of from about 30 to 250 mg per liter of the composition;
 (e) an acriflavine compound in a concentration of from about 0.5 to 5.0 mg per liter of the composition;
 (f) the cadmium compound, the fluoride compound and the flavine compound all present in a concentration sufficient to inhibit the substantially full growth of interfering microorganisms, but in a concentration insufficient to inhibit the substantial growth of *Actinomyces viscosus* or *Actinomyces naeslundii*.

28. The composition of claim 27 which includes from about 0.5 to 5.0 mg per liter of composition of an alkali metal or alkaline earth metal tellurite compound.

29. The composition of claim 27 which includes from about 0.15 to 0.5 mg per liter of composition of basic fuchsin.

* * * * *